United States Patent [19]

Daniel et al.

[11] Patent Number: 4,853,090
[45] Date of Patent: Aug. 1, 1989

[54] LITHIUM ION-SELECTIVE COMPOSITIONS, ELECTRODES AND A METHOD OF USE

[75] Inventors: Daniel S. Daniel, Rochester; Mary H. Delton, Honeoye Falls; Harold C. Warren, III, Rush, all of N.Y.

[73] Assignee: Eastman Kodak Company, Rochester, N.Y.

[21] Appl. No.: 187,175

[22] Filed: Apr. 28, 1988

[51] Int. Cl.$^4$ ............................................. G01N 27/30
[52] U.S. Cl. ................................... 204/1 T; 204/418; 546/88
[58] Field of Search ................. 204/418, 1 A; 546/88

[56] References Cited

U.S. PATENT DOCUMENTS

| | | | |
|---|---|---|---|
| 3,483,112 | 12/1969 | Ross ..................................... | 204/195 |
| 3,691,047 | 9/1972 | Ross et al. ........................... | 204/195 |
| 4,168,219 | 9/1979 | Hiiro et al. .......................... | 204/195 |
| 4,214,968 | 7/1980 | Battaglia et al. .................... | 204/195 |

FOREIGN PATENT DOCUMENTS 989441 of 0000 U.S.S.R. .
1124214 of 0000 U.S.S.R. .

OTHER PUBLICATIONS

Prabhu et al., *Anal. Chem.* 59(8), pp. 1074–1078 (1987).
Chem. Abstract 106:95038n, Rogatinskaya et al., *Ionnyi Obmen Ionometriya*, 5, pp. 188–195 (1986).
Chem. Abstract 100:78981y, Petrukhin et al., *Zh. Anal. Khim.*, 38(11), pp. 1992–1997 (1983).
Sugihara et al., *Chem. Letters*, 1987 (12), pp. 2391–2392.

*Primary Examiner*—G. L. Kaplan
*Attorney, Agent, or Firm*—J. Lanny Tucker

[57] ABSTRACT

An analytical composition, electrode and method are useful for the detection of lithium ions in an aqueous liquid. The lithium ion-selective composition comprises a lipophilic group-substituted 1,10-phenanthroline, a compound capable of solvating the phenanthroline, and a supporting matrix. This composition can be used in a lithium ion-selective electrode as a lithium ion-selective membrane. The electrode can also comprise an internal reference electrode.

26 Claims, No Drawings

LITHIUM ION-SELECTIVE COMPOSITIONS, ELECTRODES AND A METHOD OF USE

RELATED APPLICATION

Reference is made herein to copending and commonly assigned U.S.S.N. 188,519, filed on even date herewith by Delton et al and entitled "Substituted 1,10-Phenanthrolines".

FIELD OF INVENTION

This invention relates to clinical chemistry and particularly to lithium ion-selective compositions and electrodes. It also relates to methods of using the electrodes to potentiometrically determine lithium ions in aqueous liquids, for example, biological fluids.

BACKGROUND OF THE INVENTION

In the diagnosis and treatment of various diseases as well as in preventative health care, it is important to monitor the concentrations of certain ions (for example cations) in a patient's body. One cation which has merited considerble attention in the treatment of patients suffering from manic-depressive psychosis is lithium ion. Ohter instances where monitoring the concentration of this ion is important is in the treatment of alcoholics.

One type of electrode useful for determining the concentration of various ions, such as lithium, potassium, sodium, calcium and other cations in a fluid is generally composed of a reference electrode of some type and an ion-selective membrane. The reference electrode is a half-cell which contributes to providing a detectable potential during an assay. The ion-selective membrane can be made of glass or a polymeric binder material and is impregnated with an ion-sensitive carrier and a solvent for the carrier. The ion-sensitive carrier, also known as an ionophore, is a compound which is capable of sequentially complexing the desired ion, and transporting it across the membrane interface.

A significant advance in the art is the dry-operative electrode described in U.S. Pat. No. 4,214,968 (issued July 29, 1980 to Battaglia et al). The electrodes described therein have the advantage of providing reproducible potentiometric determinations of ion activity with no requirement for wet storage or preconditioning prior to use. This patent describes the electrodes as having a dried electrolyte layer comprising a solid salt dispersed in a hydrophilic binder. This electrolyte layer is also known in the art as a reference layer. Lithium ion-selective electrodes are described having cyclic polyethers as the ion carriers (Col. 16, lines 14–17).

Crown ethers have also been used as lithium ion carriers in lithium ion-selective membranes, as described for example by Kitazawa et al, *Analyst*, 110, pp. 295–299 (1985), and Kimura et al, *J. Chem. Soc. Chem. Commun.*, pp. 669–700 (1985).

Phenanthrolines are known to complex and form coordination compounds with various cations, including alkali metal ions, alkaline earth metal ions and copper to name a few. For example, Pfeiffer et al (*Zeitschrift fur anorganische und allgemeine Chemie*, 239, pp. 133–144, 1938) describe the preparation of lithium complexes with a perchlorate of o-phenanthroline. Also, an abstract of U.S.S.R. Pat. 1,124,214 (published Nov. 15, 1984) describes a magnesium ion-selective membrane composition comprising a complex of magnesium and a phenanthroline modified with a tetraphenyl borate (as the membrane active compound) and a carrier solvent. The magnesium-phenanthroline complex appears to be the matrix for the ion-selective borate compound. An abstract of U.S.S.R. 989,441 (published Jan. 15, 1983) describes the use of bis(2,9-dimethyl-1,10-phenanthroline)cupripicrate in a copper(I) ion-selective membrane and electrode.

U.S. Pat. No. 3,483,112 (issued Dec. 9, 1969 to Ross) describes an anion-selective electrode sensitive to perchlorate, halide, nitrate and other anions. The selectivity is allegedly obtained using an ion exchanger liquid comprising a salt of the anion and a metal (such as copper, iron or cobalt) complexed with an oleophilic group-substituted phenanthroline.

Lithium ion-selective compositions and electrodes are described by Sugihara et al (*Chem. Letters*, 12, pp. 2391–2392, Dec., 1987) wherein 2,9-dimethyl- and 2,9-di-n-butyl-1,10-phenanthrolines are used as ionophores. Research in this area continues to provide highly accurate assays for lithium ion which can be used in clinical environments with high confidence.

SUMMARY OF THE INVENTION

The present invention provides a lithium ion-selective composition comprising a lipophilic group-substituted 1,10-phenanthroline, a compound capable of solvating the phenanthroline, and a supporting matrix.

The composition described above can be used as a lithium-ion selective membrane in a lithium ion-selective electrode. More particularly, a lithium ion-selective electrode comprises:

(a) a reference electrode in contact with (b) a reference compositon which is, in turn, in contact with one side of (c) the lithium ion-selective composition described above.

Further, a method for the potentiometric determination of lithium ions in an aqueous liquid comprises the steps of:

A. contacting a sample of a fluid suspected of containing lithium ions with the membrane of the electrode described above, B. connecting the electrode to a second reference electrode, and C. detecting and comparing the electrical potentials generated by lithium ions in contact with the electrodes.

The present invention provides a composition, electrode and method useful for the determination of lithium ions in a highly accurate manner. In particular, the composition and electrode are highly selective for lithium ions in the presence of other cations, such as sodium, potassium and calcium. These advantages are achieved by using specific 1,10-phenanthroline compounds having one or more lipophilic substituents as lithium ion ionophores.

DETAILED DESCRIPTION OF THE INVENTION

In general, the electrodes of the present invention are prepared using components and methods described in detail in U.S. Pat. No. 4,214,968, noted above, the disclosure of which is incorporated herein in its entirety. Since most of the details are disclosed in that patent, the present disclosure will be directed to general summaries of the electrode components. As used herein, the terms "dry-operative" and "dried" have the meanings defined in U.S. Pat. No. 4,214,968.

The electrodes can also be constructed according to the teachings of Japanese Patent Publications 57(1982)-017851 and 57(1982)-017852.

The electrodes and devices of this invention can be used to determine the concentration of lithium ions in any aqueous liquid, including wastewater, cooling water, groundwater, food and brewery processing fluids, and the like. They are particularly useful for the assay of biological fluids, e.g. blood sera and urine.

The electrode of the present invention can comprise an internal reference electrode which exhibits a reproducible reference potential against which the potential occurring at the interface between the ion-selective electrode and the solution under test is measured.

Generally, the reference electrode comprises a conductive metal layer of a suitable conductive metal (for example, silver, mercury, platinum, nickel and the like). The conductive layer is in contact with a metal salt layer which may comprise substantially any insoluble salt of the metal in the conductive layer which establishes a fixed interfacial potential with the metal of the conductive layer. Preferably, the metal salt layer comprises a salt of the metal which is a product of oxidation of the metal, for example, a silver halide, or mercury halide. Such layers and techniques for making them are well known and described in more detail in U.S. Pat. No. 4,214,968, noted above. Useful metal/metal salt electrodes include silver/silver halide and mercury/mercury chloride electrodes. Other useful reference electrodes are known in the art. A silver/silver halide reference electrode is preferred in the practice of this invention.

The lithium ion-selective electrodes of this invention can also comprise a dried electrolyte or reference layer in contact with the reference electrode. In one embodiment, the dried reference layer contains the dried residue of a salt and any optional addenda (surfactants or buffers), but is binderless (according to U.S. Pat. No. 4,571,293, issued Feb. 18, 1986 to Seshimoto et al).

According to a preferred embodiment, the reference layer is a dried hydrophilic layer comprising one or more dried hydrophilic binder materials, one or more salts uniformly distributed in the binder materials, and any optional addenda (such as surfactants or buffers). Preferably, the anion of one of the salts is common to the salt of the metal salt layer of the reference electrode, and at least a portion of the cation of the salt is lithium. The amounts and types of each component of the dried reference layer and the methods of preparation are readily determined by a skilled worker in the art in view of the teachings of U.S. Pat. No. 4,214,968, noted above, and Japanese Patent Publication 58(1983)-102146.

The dried reference layer is in contact with a lithium-ion selective membrane composition. This composition is laminated, coated or otherwise applied directly over the reference layer.

Generally, the composition of this invention comprises a 1,10-phenanthroline compound (described below) as an ionophore for lithium ions, a compound capable of solvating the ionophore (described below) and a supporting matrix comprised of one or more binder materials. The matrix can be any material which, in combination with the ionophore and solvating compound, is capable of forming a thin film of sufficient permeability to produce lithium ion mobility. Useful materials include porous glass, pressed fibers, and synthetic and natural polymeric materials, such as poly(vinyl chloride), carboxylated poly(vinyl chloride), poly(styrene-co-styrene sulfonic acid), poly(vinyl chloride-co-styrene sulfonic acid), poly(vinyl chloride-co-styrene carboxylic acid) and the like. Poly(vinyl chloride) is a preferred binder material in the practice of this invention.

The ionophore is solvated by one or more organic solvents which are capable of at least partially solvating the ionophore and providing lithium ion mobility. If a hydrophobic binder is used as the supporting matrix, the solvent must be compatible with the binder. The solvent is sometimes identified in the art as a carrier solvent. Useful carrier solvents include phthalates, sebacates, aromatic and aliphatic ethers, phosphates, mixed aromatic aliphatic phosphonates, adipates, nitrated ethers or esters or mixtures thereof, and others known in the art. Particularly useful solvents include, but are not limited to, dibutyl sebacate, bromophenyl phenyl ether, bis(2-ethylhexyl) sebacate, bis(2-ethylhexyl) 4-nitrophthalate, o-nitrophenyl valerate, dioctyl phenylphosphonate, o-nitrophenyl phenyl ether, o-nitrophenyl octyl ether, triisodecyl trimellitate, dimethyl phthalate, diisodecyl phthalate, tris(2-ethylhexyl) phosphate, and mixtures thereof.

In addition, the composition of this invention can include one or more salts of oleophilic anions, such as a tetraaryl borate (for example, tetraphenyl borate). This salt can be present in amounts up to about 33 mole percent based on the amount of 1,10-phenanthroline present, and preferably from about 10 to about 25 mole percent.

The composition can also comprise one or more surfactants (such as a TRITON surfactant available from Rohm and Haas, DC-510 available from Dow Chemical), and other optional addenda which do not interfere with lithium ion transport or selectivity.

The ionophores useful in the materials of this invention are oleophilic group-substituted 1,10-phenanthrolines. These phenanthrolines are substituted in at least one of the ring positions, and preferably they are substituted in at least one of the 2- and 9-positions of the ring, with at least one group or fused ring which contributes to the oleophilic nature of the compound and to complexing with a lithium ion. The compounds are insoluble in water and capable of being solvated by the carrier solvents described above. The phenanthrolines useful in this invention are used in "free" or uncomplexed form. In other words, they are not complexed to metal or other cations, or to anions. Generally, they are represented by the formula (I):

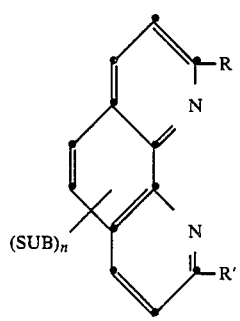

wherein R and R' are independently hydrogen or oleophilic monovalent organic groups, provided that both R and R' are not hydrogen unless n (defined below) is greater than 0. Useful organic groups include, but are not limited to, substituted or unsubstituted alkyl of 1 to 20 carbon atoms (such as methyl, ethyl, 2-chloroethyl, n-propyl, isopropyl, t-butyl, n-pentyl, 2-octyl, 2-ethylhexyl, methoxymethyl and dodecyl), substituted or unsubstituted cycloalkyl of 5 to 10 carbon atoms (such as cyclopentyl and cyclohexyl), including bridged cycloalkyl groups, and cycloalkyl groups having side chains or side rings (such as bicyclo[3.1.0]hexane), substituted or unsbustituted aryl of 6 to 14 carbon atoms in the ring system, including fused ring systems [such as phenyl, naphthyl, 3,5-methoxyphenyl, 2-methoxy-3-(2-methoxyphenyl)phenyl, biphenylyl and binaphthylyl], and one or more alkyl, cycloalkyl or aryl as defined above which are interrupted with one or more oxy, thio or amino groups.

Also, one or both of R and R' can form a substituted or unsbustituted fused ring with the phenanthroline nucleus. Such fused rings can comprise from 3 to 5 carbon or hetero atoms in addition to those in the nucleus. Further, R and R' together can form a macrocyclic fused ring attached to the phenanthroline nucleus (such as catenanes or crown phenanthrolines).

In formula (I) above, SUB represents additional substituents which can be any of the alkyl, cycloalkyl or aryl groups defined above for R and R', or they can be halo groups (such as fluoro, chloro or bromo). Preferably, SUB is substituted or unsubstituted alkyl of 1 to 6 carbon atoms (as defined above) or substituted or unsubstituted aryl of 6 to 10 carbon atoms (as defined above). Also, n is from 0 to 6, but it is greater than 0 if both of R and R' are hydrogen.

In preferred embodiments, R and R' are independently substituted or unsubstituted alkyl, substituted or unsubstituted cycloalkyl, or substituted or unsubstituted aryl as defined above, SUB is substituted or unsubstituted alkyl or substituted or unsubstituted aryl as defined above, and n is 1 to 2.

Preferred novel substituted 1,10-phenanthrolines are described and claimed in U.S.S.N. 188,579 of Delton et al, noted above. In general, these preferred compounds are represented by the structure (II):

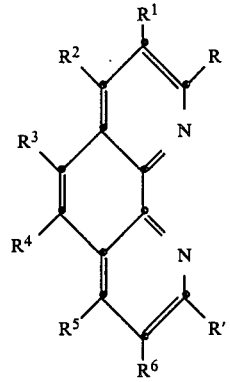

II wherein

R is selected from the group consisting of substituted or unsubstituted alkyl having a molecular weight of at least 45, substituted or unsubstituted cycloalkyl having 5 to 10 carbon atoms in the ring and substituted phenyl, R' is either hydrogen, halo or independently of R, selected from the groups defined for R, $R^1$, $R^2$, $R^3$, $R^4$, $R^5$ and $R^6$ are independently hydrogen, substituted or unsubstituted alkyl of 1 to 10 carbon atoms, substituted or unsubstituted cycloalkyl of 6 to 10 carbon atoms, substituted or unsubstituted aryl of 6 to 14 carbon atoms or halo groups, provided that R' is not hydrogen when R is substituted or unsubstituted alkyl as defined above, and further provided that when R and R' are both either n-butyl-, t-butyl- or alkyl-substituted phenyl as defined above, at least one of $R^1$, $R^2$, $R^3$, $R^4$, $R^5$ and $R^6$ is alkyl, cycloalkyl, aryl or halo as defined above.

The following nonlimiting list shows representative phenanthrolines (I–XXVII) useful in the practice of this invention:

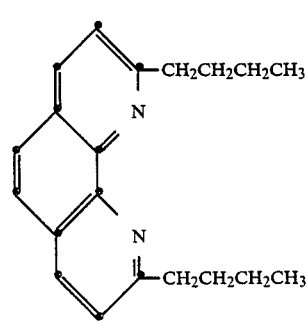

I

-continued
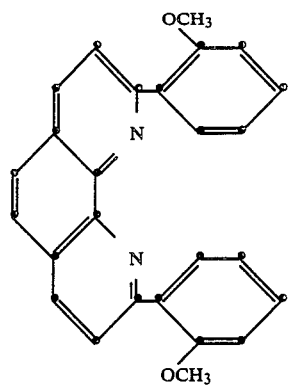
II
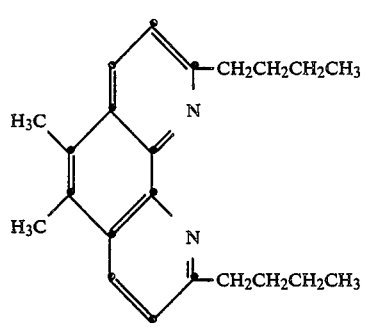
III
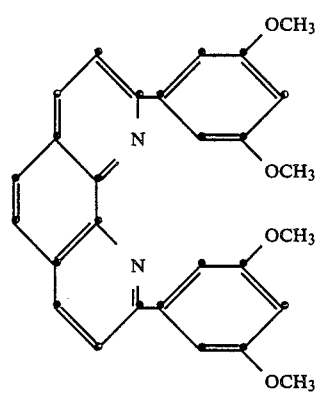
IV
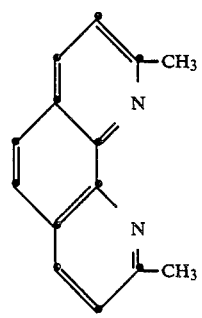
V

-continued
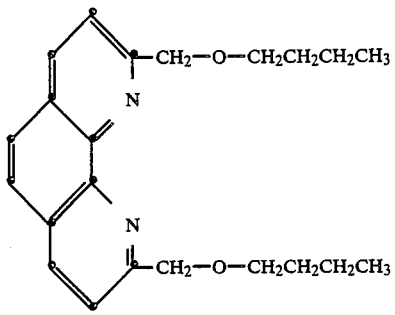
VI
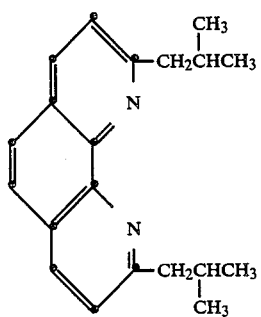
VII
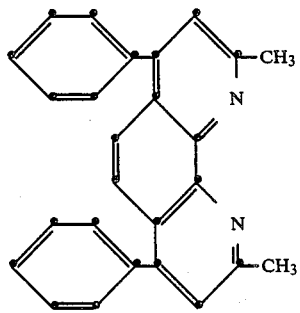
VIII
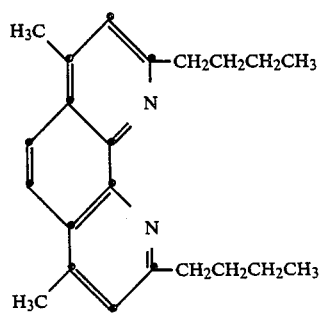
IX

-continued
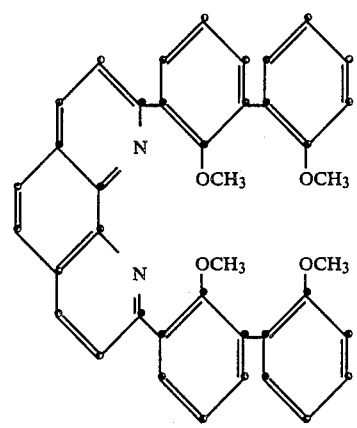
X
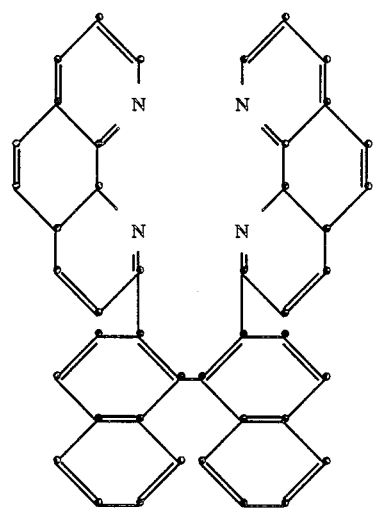
XI
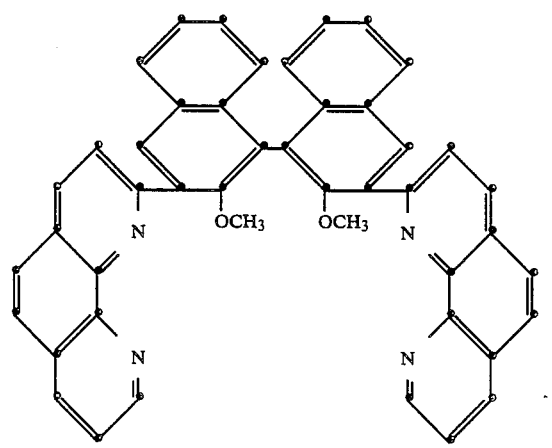
XII

-continued
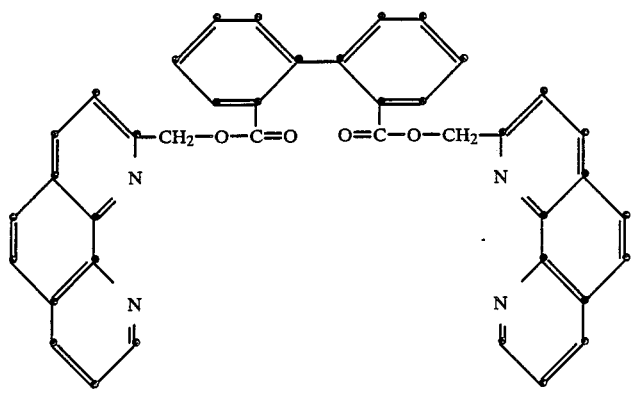
XIII
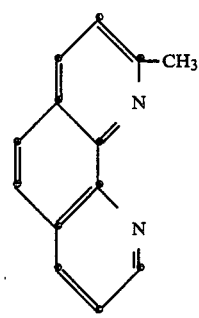
XIV
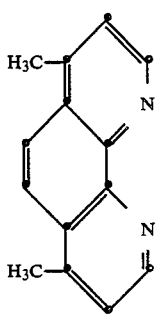
XV
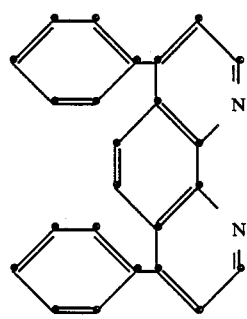
XVI

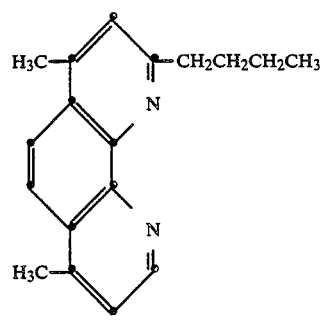
XVII
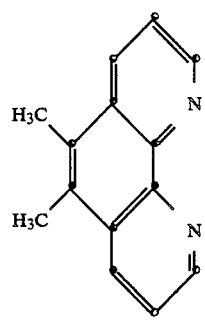
XVIII
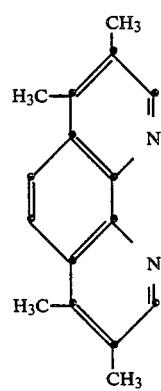
XIX
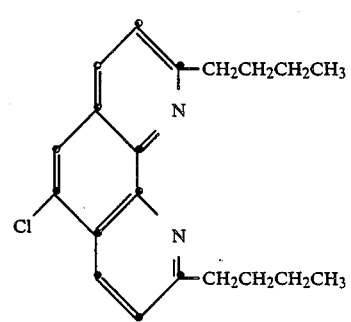
XX

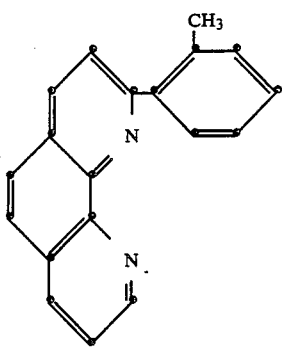
XXI
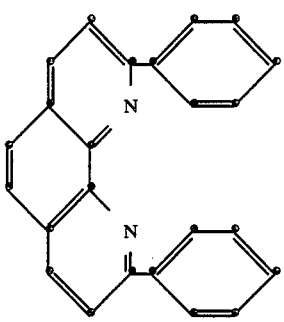
XXII
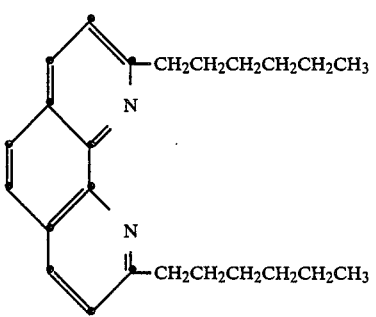
XXIII
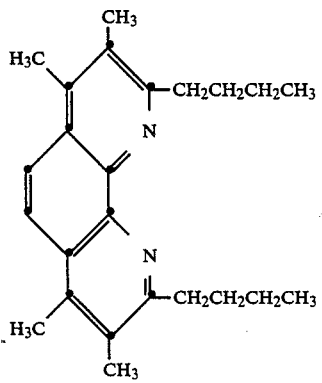
XXIV

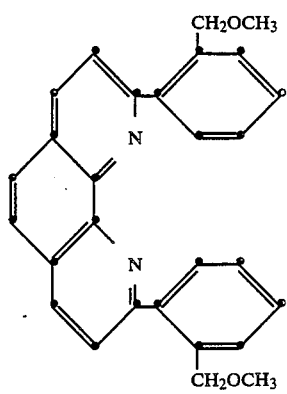

XXV

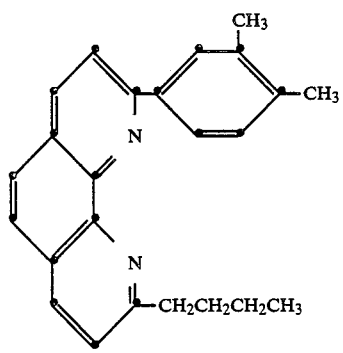

XXVI

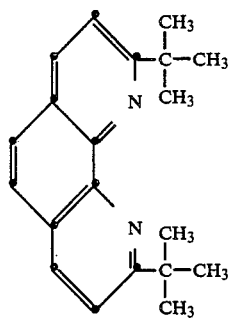

XXVII

Of the compounds shown above, Compounds I, III, VII, IX, XX, XXIII and XXVI are preferred for use as lithium ionophores. Compounds III and IX are most preferred.

Some of the 1,10-phenanthroline compounds useful herein can be purchased from commercial sources, such as Aldrich Chemical and Eastman Kodak Co. Others can be prepared using known starting materials and procedures, as described herein and by Dietrich et al, *Tetra. Letters*, 5091, 1983. Other 1,10-phenanthrolines useful herein are novel and are prepared, as described below in the illustrated preparatory procedures and in U.S.S.N. 188,579 of Delton et al, noted above and incorporated herein by reference.

In the membrane composition described above, generally, the 1,10-phenanthroline is present in an amount of from about 0.1 to about 1.5, and preferably from about 0.2 to about 0.8 g/m² of coated surface area. The amount of solvating compound will vary depending upon which solvent and phenanthroline are used, but generally, it is present in an amount sufficient to solvate the phenanthroline. Generally more solvent is used than is necessary to solvate the phenanthroline so that it remains solvated under a variety of storage conditions. A 100 to 500 percent excess on a weight basis is useful.

Usually the amount of solvating compound is from about 2 to about 24 g/m².

The amount of supporting matrix which is present is determined by the desired thickness of the membrane and by the necessity for providing support for the phenanthroline-solvent dispersion. The membranes generally have a thickness in the range of from about 2 to about 20 μm. Generally, an amount of from about 2 to about 24 g/m² is useful.

Membranes including hydrophobic binder materials, an ionophore and solvating solvents are prepared using known film-coating or casting techniques. The amounts of each membrane component, including optional addenda, are described above and readily determined from the art.

The electrodes of this invention can be self-supporting, meaning that one or mroe layers of the electrode have sufficient mechanicl strength to support the remaining portions of the electrode. Preferably, however, they further include a support which may be comprised of any material capable of bearing, either directly or by virtue of some intervening adhesion-improving layer, the other necessary portions of the electrode described herein. The support may be porous or nonporous and be composed of wood, cellulose, ceramic, metal, glass, filter paper, polymeric or glass fibers, polymeric films and the like. Preferably, the support is prepared from a nonporous polymeric film.

Lithium ion activity can be measured with the electrode of the present invention by measuring the steady-state difference in electrical potential between the fluid to be tested (test fluid) and a reference fluid in a cell arrangement schematically represented by the following:

Reference electrode 1/test fluid//membrane//reference fluid/reference electrode 2. The calculations required to determine the ionic activity of the test fluid are derived from the well-known Nernst equation and are known to a skilled worker in the art.

The electrode of this invention incorporates within its structure substantially all of the components needed for making a potentiometric determination with the exception of a second reference electrode, a potential-indicating device (for example, an electrometer or potentiometer) and associated wiring. In use, the user merely contacts the membrane of the electrode with a sample of the test fluid (for example, less than 200 µl) and connects the electrodes to a potential-indicating device. Contacting the fluid with the membrane can be done in any suitable manner, but preferably, a sample of the test fluid is applied to the membrane with a suitable dispensing means. Second reference electrodes for use in the assay, such as standard calomel electrodes, are well known. Similarly, electrometers are well known.

Alternatively and preferably, two or more electrodes of the present invention are incorporated or mounted into a frame to form a single device or test slide as it is sometimes known in the art. One of the electrodes is used to contact the test fluid while another is used as the second reference electrode to which the reference solution is contacted. Such a device is described in more detail in U.S. Pat. No. 4,171,246, (issued Oct. 16, 1979 to Hamblen et al). Such devices generally comprise a means for providing a liquid junction between the electrodes, including a capillary bridge formed of a strip of paper, a standard chromatographic strip, a strip of a porous polymeric film, natural or synthetic threads or fibers. Reference fluids useful in practicing the present invention are known in the art and commercially available.

In the preparatory procedures and examples which follow illustrating the practice of the invention, the materials used in constructing the electrode were obtained as follows:

DC-510 polysilicone surfactant from Dow Corning, SURFACTANT 10G nonionic surfactant from Olin Corporation, Poly(vinyl chloride), chromatographic grade (Polyscience Co.), and the remainder from Eastman Kodak Co. or prepared using standard starting materials and known procedures.

Preparation 1

Preparation of 2,9-di-n-butyl-1,10-phenanthroline (Compound I)

1,10-Phenanthroline monohydrate (0.83 g, 4.2 mmolar) was dissolved in 25 ml of freshly distilled tetrahydrofuran in a flask equipped for magnetic stirring and having an argon inlet. The contents were cooled in an iced water bath and n-butyl lithium (10 ml of 2.1 molar solution in hexane) was added dropwise with a syringe through a septum attached to the flask. An immediate color change to dark black-purple and then to bright yellow occurred upon addition of each drop of n-butyl lithium until about 2 ml had been added. Thereafter, the solution remained a dark purple color. When all of the n-butyl lithium had been added, the cold bath was removed and the reaction mixture allowed to warm to room temperature overnight.

After recooling the reaction mixture, it was quenched by the addition of methanol (a few ml) and then oxidized by the addition of a solution of iodine (9 g in 30 ml tetrahydrofuran) for 30 minutes. After an additional 60 minutes of stirring, the crude product was isolated by pouring the reaction mixture into saturated sodium bisulfite solution and extracting with a mixture of ethyl ether and dichloromethane. The extracts were washed sequentially with bisulfite solution, water and brine, and then dried over anhydrous sodium sulfate. Removal of solvent under reduced pressure gave a dark oil which was purified by chromatogrpahy on silica gel using dichloromethane as eluant. In this manner, 0.7 g of the desired phenanthroline was obtained.

Preparation 2

Preparation of 2,9-Di-n-butyl-5,6-dimethyl-1,10-phenanthroline (Compound III)

Compound III was prepared similarly to Compound I above except that the 1,10-phenanthroline monohydrate starting material was substituted with methyl groups in the 5- and 6- positions.

Examples 1-4

Lithium Ion-Selective Electrodes

This example illustrates four lithium ion-selective electrodes of the present invention. Each electrode was prepared having the format and components shown below:

| | | |
|---|---|---|
| Membrane | Poly(vinyl chloride) | 4-15 g/m$^2$ |
| | o-nitrophenyl octyl ether | 5-18 g/m$^2$ |
| | 1,10-Phenanthroline (see below) | 0.2-0.8 g/m$^2$ |
| | DC-510 TM silicone surfactant | 0.01-0.08 g/m$^2$ |
| | Gelatin | 3-12 g/m$^2$ |
| | Sodium chloride | 1-6 g/m$^2$ |
| Reference Layer (pH 4-8) | Lithium nitrate | 0.3-2 g/m$^2$ |
| | SURFACTANT 10G nonionic surfactant | 0.04-0.1 g/m$^2$ |

The 1,10-phenanthroline compounds used in these electrodes are listed below:

| | |
|---|---|
| Example 1 | Compound III |
| Example 2 | Compound I |
| Example 3 | Compound VII |
| Example 4 | Compound IX |

Example 5

Determination of Lithium Ions

Several electrodes of this invention were used in the determination of lithium ions in an aqueous test solution. All of the electrodes were prepared as shown above in Examples 1-4.

The assays were carried out by applying a sample (5-25 µl) of a test solution containing lithium ions and another cation (as a potential interferent) to the membrane of the electrode, and the electrochemical cell was completed with a suitable external reference electrode (a silver/silver chloride electrode). Selectivity coefficients were calculated using standard calculations from the difference in potential of the cell using a 0.1 molar solution of lithium chloride and an equimolar solution of the chloride of the other ion (that is, sodium, potassium or calcium).

Table I below shows the results of the assays and determination of selectivity coefficients. A coefficient less than 1.0 indicates selectivity of lithium ions over the other cations. The lower the coefficient, the better the lithium ion selectivity. It can be seen that some 1,10-phenanthroline compounds have high selectivity of lithium ions over all cations tested, whereas other compounds exhibit lithium ion selectivity over only one or two other cations.

Novel Compounds III and IX, which are among the preferred ionophores, show an improvement in lithium ion selectivity over known Compound I in the assays illustrated herein.

TABLE I

| 1,10-Phenanthroline Compound | Selectivity Coefficients | | |
|---|---|---|---|
| | $k(Li^+/Na^+)$ | $k(Li^+/Ca^{++})$ | $k(Li^+/K^+)$ |
| I | 0.0055 | 0.0071 | 0.0044 |
| II | 1.4 | 0.44 | 1.2 |
| III | 0.004 | NT | NT |
| IV | 3.3 | NT | NT |
| V | 0.029 | 0.018 | 0.046 |
| VI | 0.98 | 0.052 | 0.064 |
| VII | 0.0073 | 0.012 | 0.058 |
| VIII | 0.12 | 0.071 | 0.10 |
| IX | 0.005 | NT | NT |
| X | 1.3 | 0.57 | NT |
| XI | 0.07 | 0.07 | 0.08 |
| XII | 0.38 | NT | NT |
| XIII | 0.22 | 0.064 | 0.33 |
| XIV | 0.16 | 0.28 | NT |
| XV | 0.08 | 0.16 | 0.046 |
| XVI | 0.05 | 0.05 | 0.02 |
| XVII | 0.02 | NT | NT |
| XVIII | 0.05 | NT | NT |
| XIX | 0.98 | NT | NT |
| XX | 0.025 | NT | NT |
| XXI | 0.14 | NT | NT |
| XXII | 0.11 | NT | NT |
| XXIII | 0.009 | NT | NT |
| XXIV | 0.90 | NT | NT |
| XXV | 0.058 | 0.00332 | 0.20 |
| XXVI | 0.019 | NT | 0.016 |
| XXVII | 1.1 | NT | NT |

In Table I, "NT" means that the electrode was not tested for that particular selectivity coefficient. Compounds IV and XXVII are within the scope of the present invention, yet they did not show selectivity for lithium ions over sodium ions. However, it is believed that further testing would show lithium ion selectivity over other alkali metal or alkaline earth ions.

The invention has been described in detail with particular reference to preferred embodiments thereof, but it will be understood that variations and modifications can be effected within the spirit and scope of the invention.

We claim:

1. A dried lithium ion-selective composition comprising an uncomplexed lipophilic group-substituted 1,10-phenanthroline, a compound capable of solvating said phenanthroline, and a supporting matrix.

2. The composition of claim 1 wherein said phenanthroline has the formula (I):

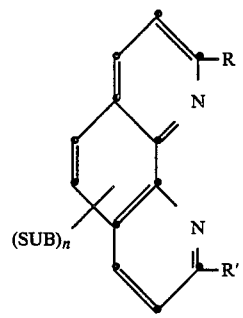

wherein n is 0 to 6, R and R' are independently hydrogen or oleophilic monovalent organic groups, or one or both of R and R' form fused rings with the phenanthroline nucleus, or R and R' together form a macrocyclic ring attached to the phenanthroline nucleus, provided that both R and R' are not hydrogen unless n is greater than 0, and SUB represents an alkyl, aryl, cycloalkyl or halo.

3. The composition of claim 2 wherein n is 1 or 2, R and R' are selected from the group consisting of alkyl of 1 to 20 carbon atoms, aryl of 6 to 14 carbon atoms, or cycloalkyl of 5 to 8 carbon atoms, and SUB is alkyl of 1 to 6 carbon atoms or aryl of 6 to 10 carbon atoms.

4. The composition of claim 1 wherein said phenanthroline has the structure (II):

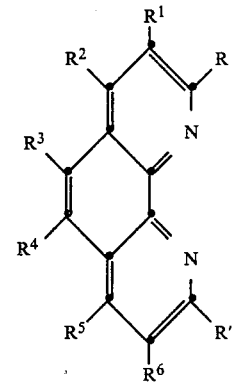

wherein
R is selected from the group consisting of alkyl having a molecular weight of at least 45, cycloalkyl having 5 to 14 carbon atoms in the ring and substituted phenyl,
R' is either hydrogen, halo or independently of R, selected from the groups defined for R,
$R^1$, $R^2$, $R^3$, $R^4$, $R^5$ and $R^6$ are independently hydrogen, alkyl of 1 to 10 carbon atoms, cycloalkyl of 6 to 10 carbon atoms, aryl of 6 to 10 carbon atoms or halo groups,
provided that R' is not hydrogen when R is alkyl as defined above, and further provided that when R and R' are both either n-butyl-, t-butyl- or alkyl-substituted phenyl as defined above, at least one of $R^1$, $R^2$, $R^3$, $R^4$, $R^5$ and $R^6$ is alkyl, cycloalkyl, aryl or halo as defined above.

5. The composition of claim 1 wherein said phenanthroline is one of the following compounds:

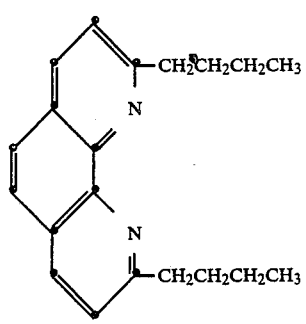
I
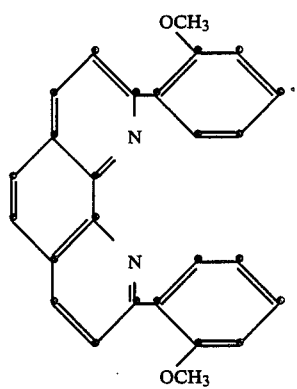
II
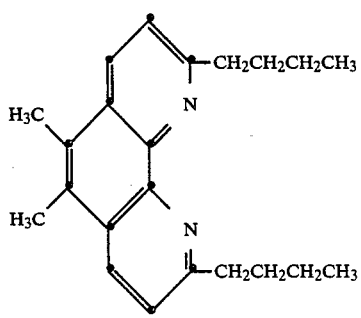
III
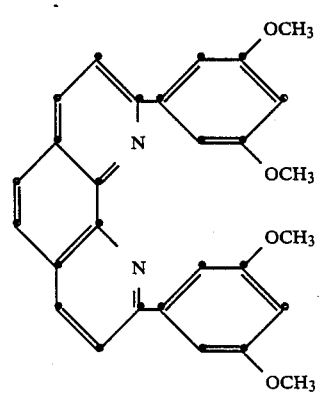
IV

-continued
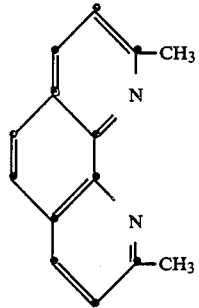
V
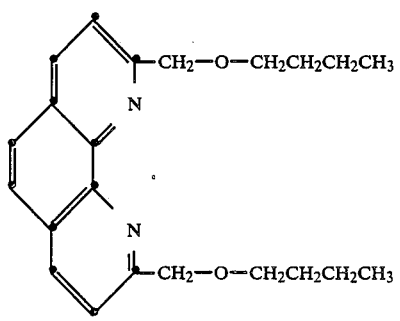
VI
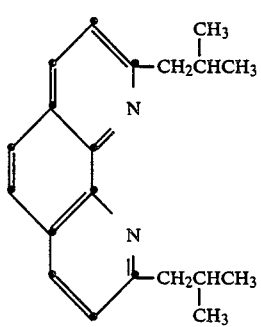
VII
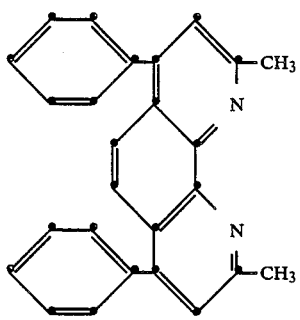
VIII
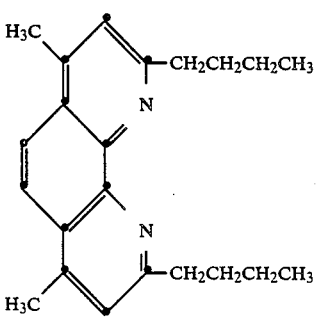
IX -continued
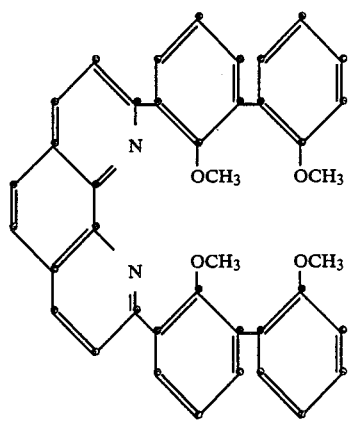
X
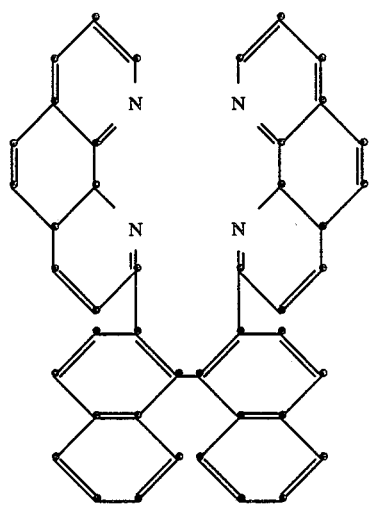
XI
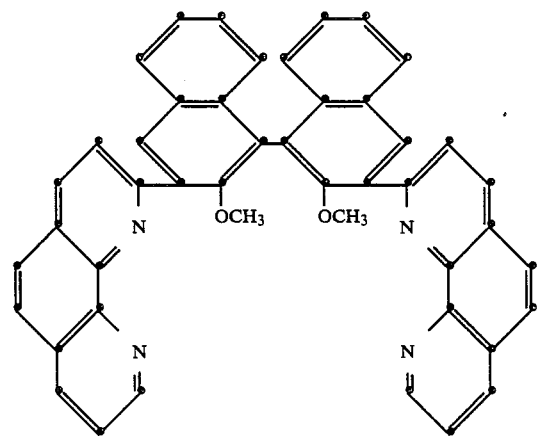
XII -continued
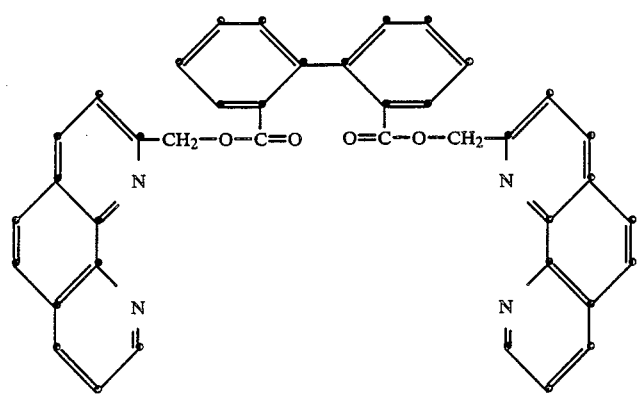
XIII
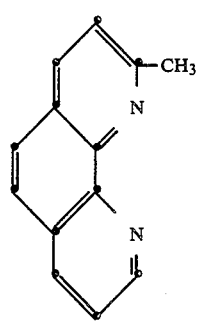
XIV
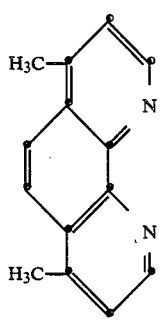
XV
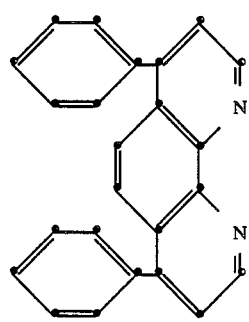
XVI -continued
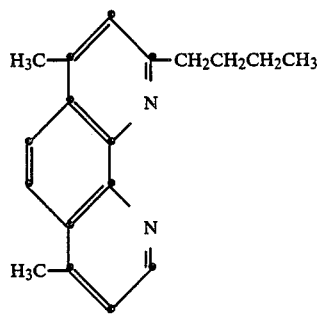 XVII
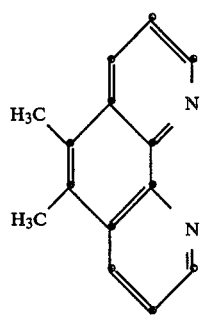 XVIII
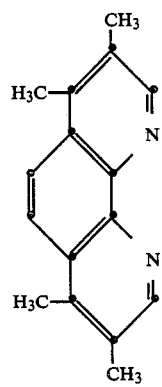 XIX
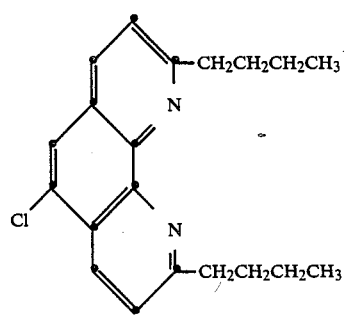 XX -continued
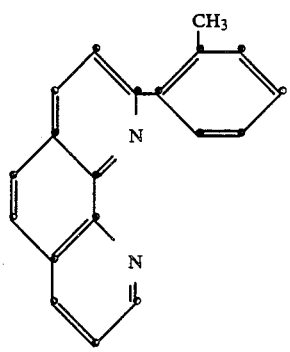
XXI
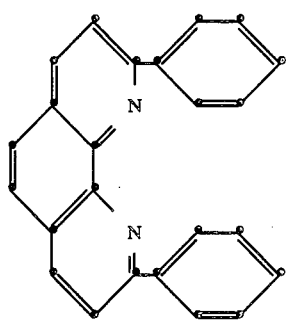
XXII
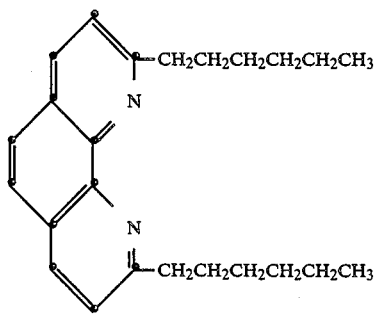
XXIII
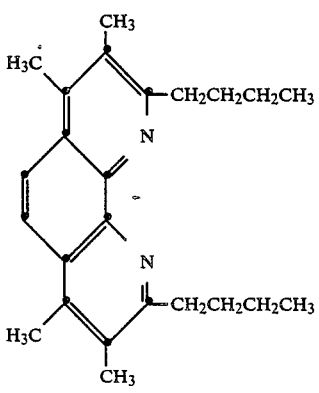
XXIV

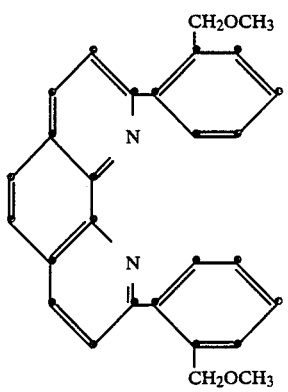

XXV

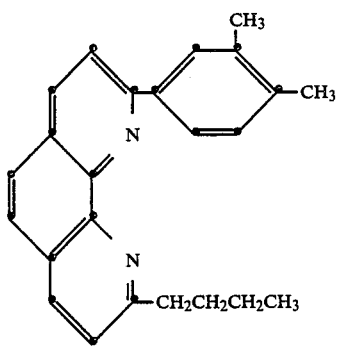

XXVI

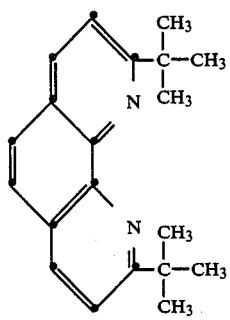

XXVII

6. The composition of claim 5 wherein said phenanthroline is Compound I, III, VII, IX, XX, XXIII or XXVI.

7. The composition of claim 6 wherein said phenanthroline is Compound III or IX.

8. The composition of claim 1 wherein said supporting matrix is a hydrophobic binder.

9. The composition of claim 8 wherein said hydrophobic binder is poly(vinyl chloride).

10. A lithium ion-selective electrode having a dried lithium ion-selective membrane composition comprising an uncomplexed lipophilic group-substituted 1,10-phenanthroline, a compound capable of solvating said phenanthroline, and a supporting matrix.

11. A lithium ion-selective electrode comprising:
    (a) a reference electrode in contact with
    (b) a reference composition which is, in turn, in contact with one side of
    (c) a dried lithium ion-selective composition comprising an uncomplexed lipophilic group-substituted 1,10-phenanthroline, a compound capable of solvating said phenanthroline, and a supporting matrix.

12. The electrode of claim 11 wherein said phenanthroline ahs the formula (I):

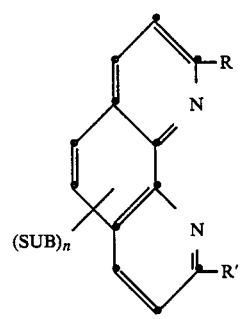

I wherein n is 0 to 6, R and R' are independently hydrogen or oleophilic monovalent organic groups, or one or both of R and R' form fused rings with the phenanthroline nucleus, or R and R' together form a macrocyclic ring attached to the phenanthroline nucleus, provided that both R and R' are not hydrogen unless n is greater than 0, and SUB is alkyl, cycloalkyl, aryl or halo.

13. The electrode of claim 12 wherein said supporting matrix is a hydrophobic binder.

14. A dry-operative lithium ion-selective electrode comprising:
   (a) a dried internal reference element comprising the dried residue of a solution of a salt and a hydrophilic polymeric binder in a solvent for the polymer and the salt and,
   (b) in contact with said reference element, a hydrophobic lithium ion-selective membrane of predetermined uniform thickness in regions thereof intended for contact with a sample for anlaysis, said membrane comprising a hydrophobic polymeric binder having distributed therein an uncomplexed lipophilic group-substituted 1,10-phenanthroline.

15. The electrode of claim 14 wherein said phenanthroline has the formula (I):

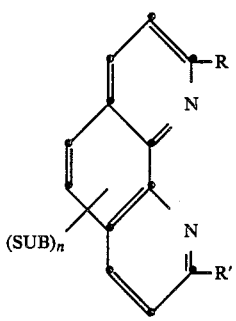

wherein n is 0 to 6, R and R' are independently hydrogen or oleophilic monovalent organic groups, or one or both of R and R' form fused rings with the phenanthroline nucleus, or R and R' together form a macrocyclic ring attached to the phenanthroline nucleus, provided that both R and R' are not hydrogen unless n is greater than 0, and SUB is alkyl, cycloalkyl, aryl or halo.

16. The electrode of claim 14 wherein said phenanthroline has the structure (II):

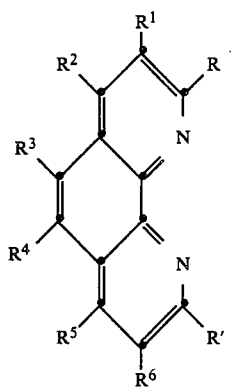

wherein
R is selected from the group consisting of alkyl having a molecular weight of at least 45, cycloalkyl having 5 to 14 carbon atoms in the ring and substituted phenyl,
R' is either hydrogen, halo or independently of R, selected from the groups defined for R,
$R^1$, $R^2$, $R^3$, $R^4$, $R^5$ and $R^6$ are independently hydrogen, alkyl of 1 to 10 carbon atoms, cycloalkyl of 6 to 10 carbon atoms, aryl of 6 to 10 carbon atoms or halo groups,
provided that R' is not hydrogen when R is alkyl as defined above, and further provided that when R and R' are both either n-butyl-, t-butyl- or alkyl-substituted phenyl as defined above, at least one of $R^1$, $R^2$, $R^3$, $R^4$, $R^5$ and $R^6$ is alkyl, cycloalkyl, aryl or halo as defined above.

17. The electrode of claim 14 wherein said phenanthroline is one of the following compounds:

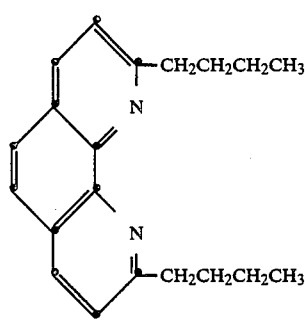

I

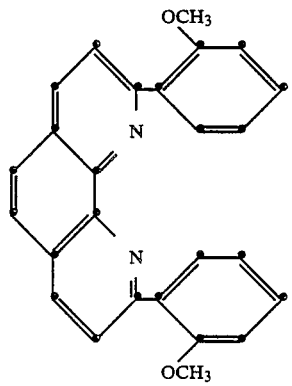

II

-continued
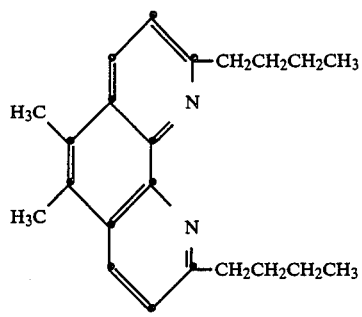
III
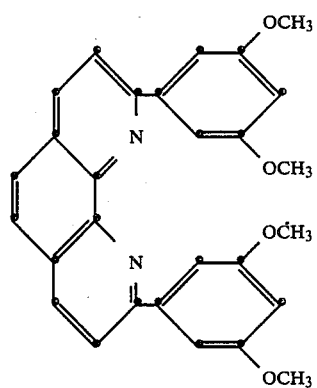
IV
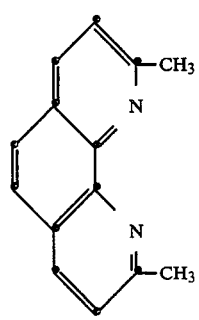
V
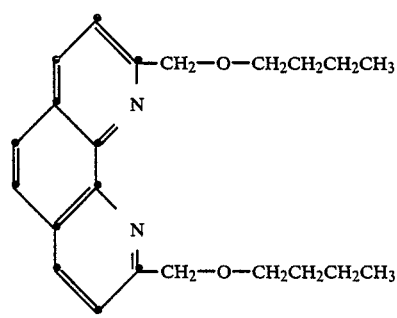
VI

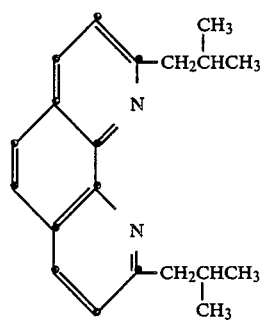
VII
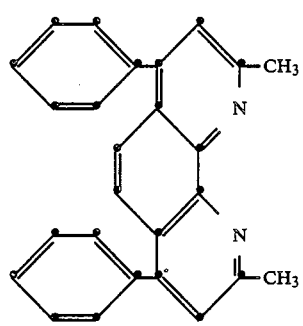
VIII
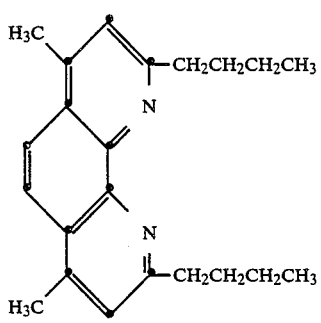
IX
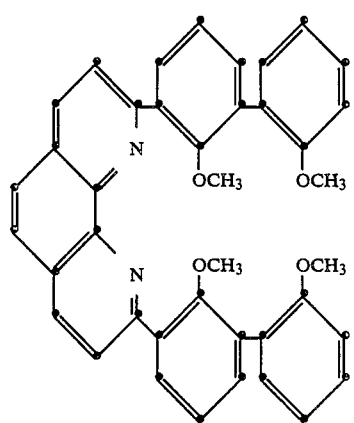
X

XI
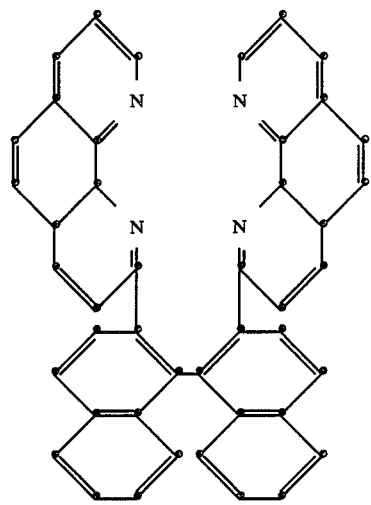
XII
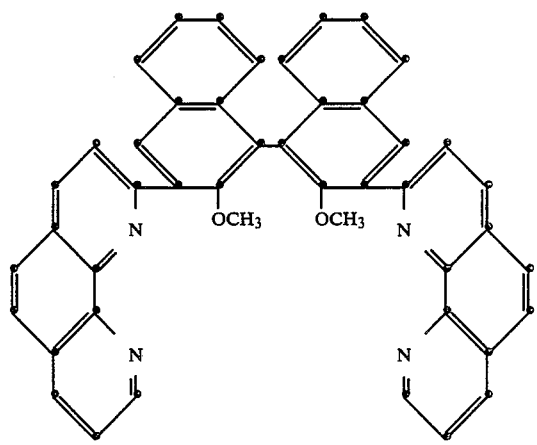
XIII
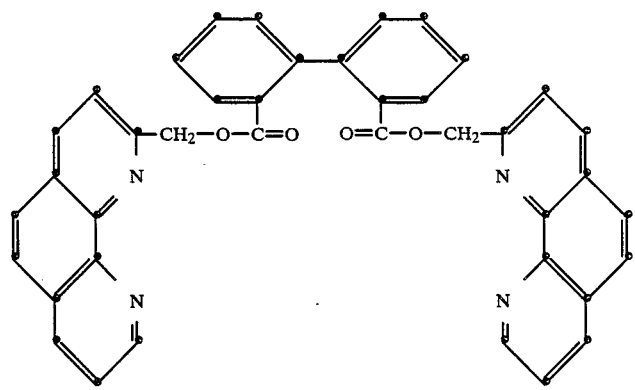
XIV
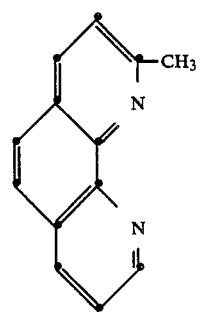

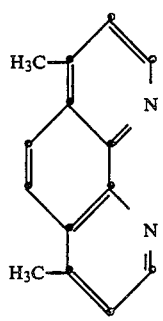
XV
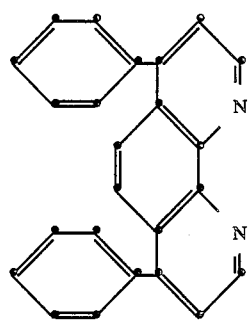
XVI
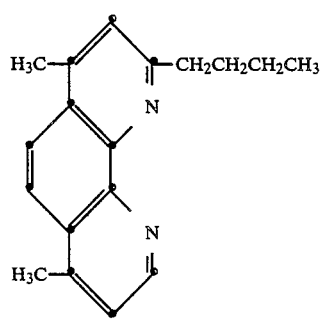
XVII
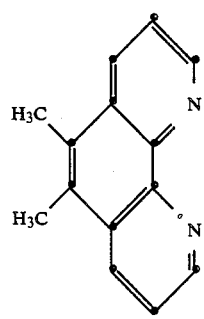
XVIII

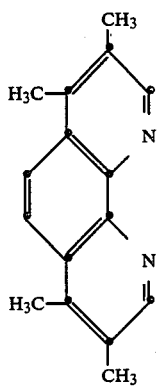
XIX
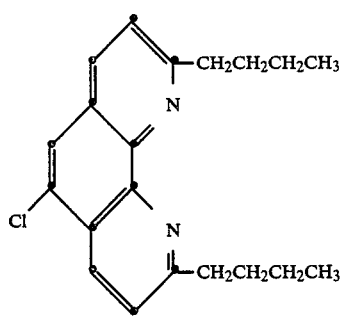
XX
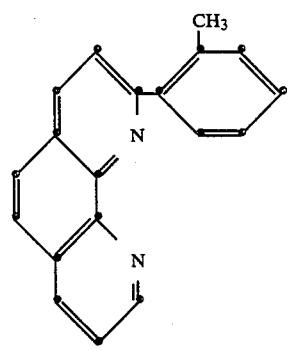
XXI
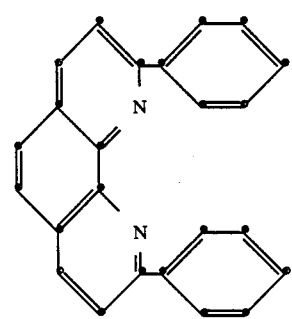
XXII

-continued
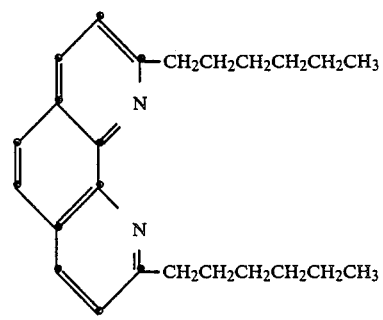
XXIII
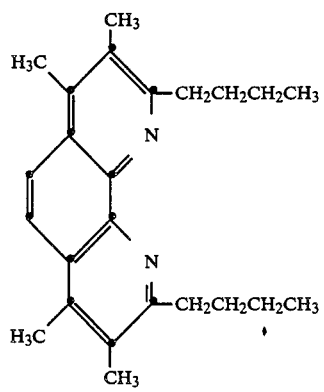
XXIV
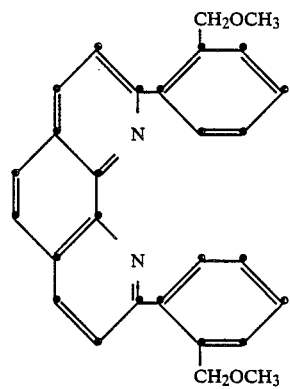
XXV
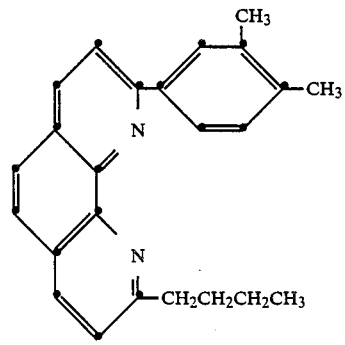
XXVI

-continued

XXVII

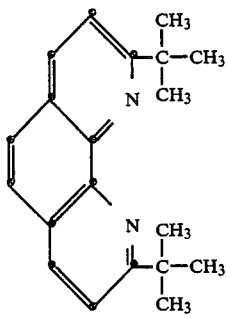

18. The electrode of claim 14 wherein said supporting matrix is a hydrophobic binder.

19. A method for the potentiometric determination of lithium ions in an aqueous liquid comprising the steps of:
   A. contacting a sample of a fluid suspected of containing lithium ions with the membrane of a lithium ion-selective electrode said membrane comprising an uncomplexed lipophilic group-substituted 1,10-phenanthroline, a compound capable of solvating said phenanthroline, and a supporting matrix,
   B. connecting said electrode to a second reference electrode, and
   C. detecting and comparing the electrical potentials generated by lithium ions in contact with said electrodes.

20. The method of claim 19 wherein both of said electrodes are mounted in a frame of a single device comprising a means for transporting lithium ions between said electrodes, and said second reference electrode is contacted with a sample of a reference fluid containing a known amount of lithium ions.

21. The method of claim 19 wherein said phenanthroline has the formula (I):

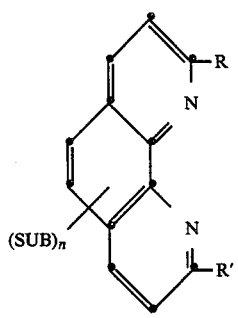

I wherein n is 0 to 6, R and R' are independently hydrogen or oleophilic monovalent organic groups, or one or both of R and R' form fused rings with the phenanthroline nucleus, or R and R' together form a macrocyclic ring attached to the phenanthroline nucleus, provided that both R and R' are not hydrogen unless n is greater than 0, and SUB represents an alkyl, aryl, cycloalkyl or halo.

22. The method of claim 21 wherein n is 1 or 2, R and R' are selected from the group consisting of alkyl of 1 to 20 carbon atoms, aryl of 6 to 14 carbon atoms, or cycloalkyl of 5 to 8 carbon atoms, and SUB is alkyl of 1 to 6 carbon atoms or aryl of 6 to 10 carbon atoms.

23. The method of claim 19 wherein said phenanthroline has the structure (II):

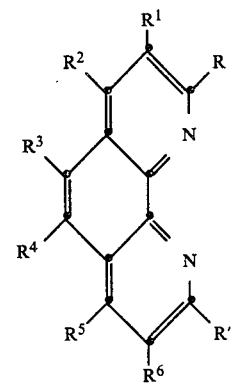

II wherein
   R is selected from the group consisting of alkyl having a molecular weight of at least 45, cycloalkyl having 5 to 14 carbon atoms in the ring and substituted phenyl,
   R' is either hydrogen, halo or independently of R, selected from the groups defined for R,
   $R^1$, $R^2$, $R^3$, $R^4$, $R^5$ and $R^6$ are independently hydrogen, alkyl of 1 to 10 carbon atoms, cycloalkyl of 6 to 10 carbon atoms, aryl of 6 to 10 carbon atoms or halo groups,
   provided that R' is not hydrogen when R is alkyl as defined above, and further provided that when R and R' are both either n-butyl-, t-butyl- or alkyl-substituted phenyl as defined above, at least one of $R^1$, $R^2$, $R^3$, $R^4$, $R^5$ and $R^6$ is alkyl, cycloalkyl, aryl or halo as defined above.

24. The method of claim 19 wherein said phenanthroline is one of the following compounds:

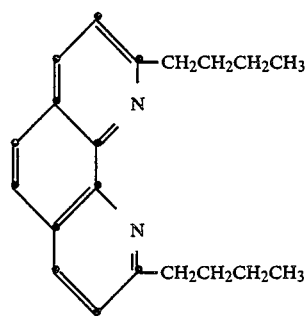 I
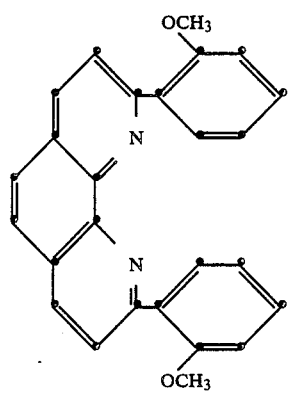 II
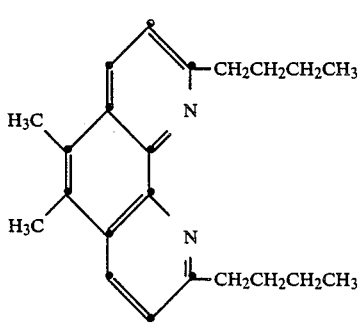 III
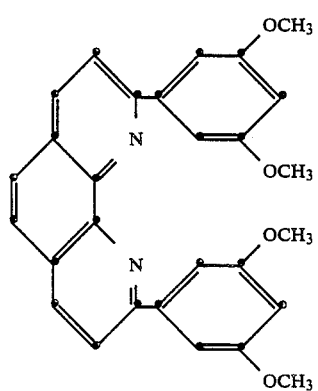 IV

-continued
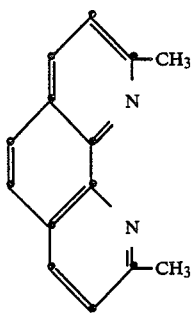 V
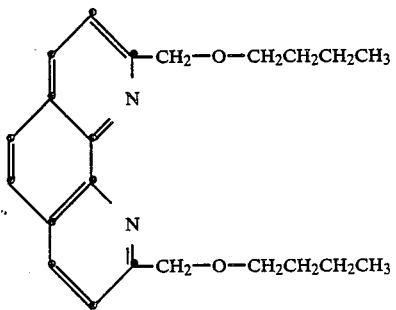 VI
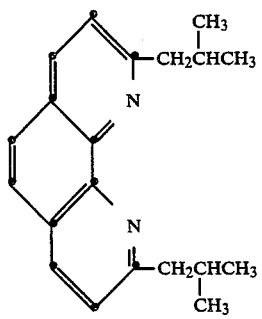 VII
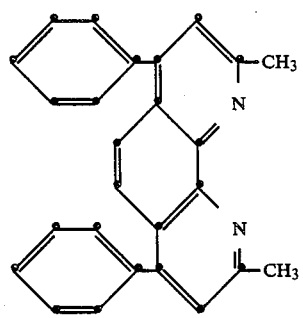 VIII
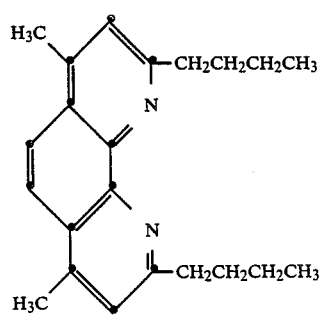 IX

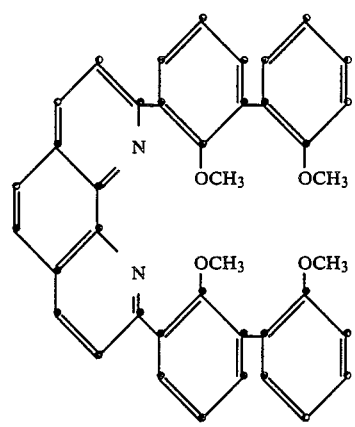
X
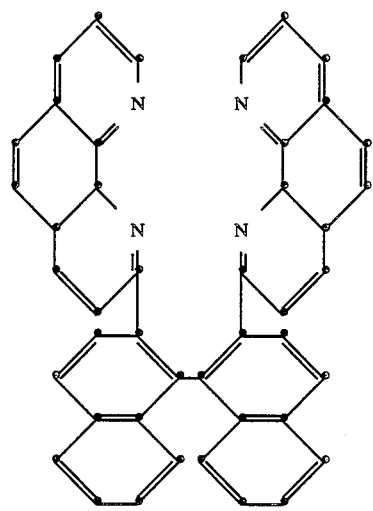
XI
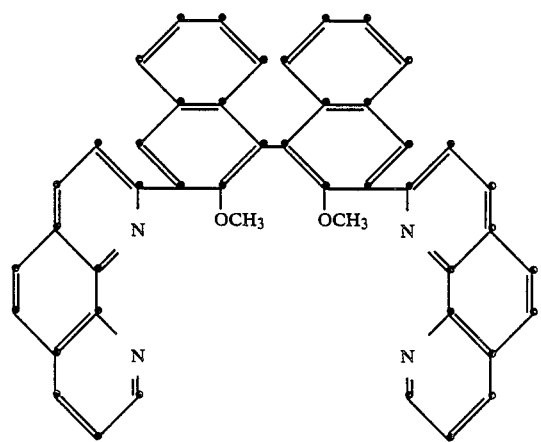
XII

-continued
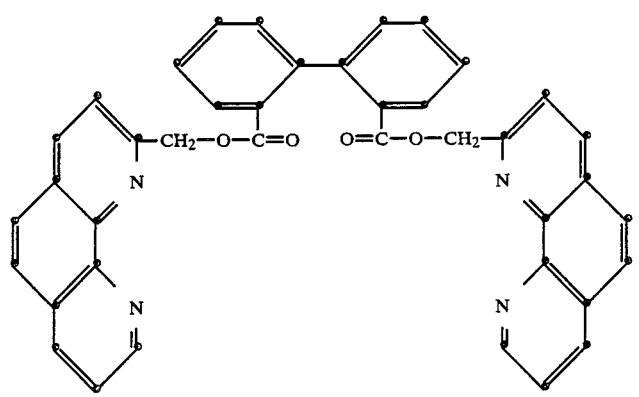
XIII
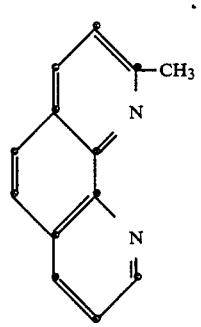
XIV
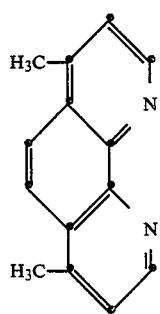
XV
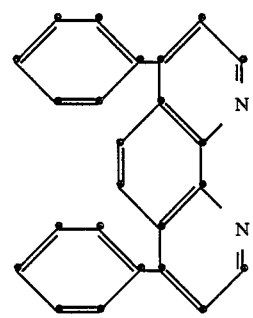
XVI

-continued
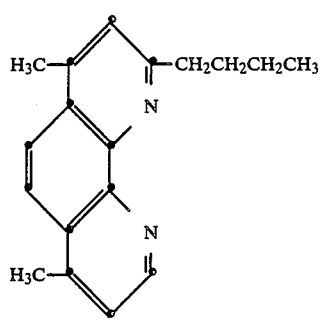
XVII
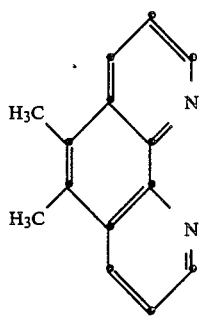
XVIII
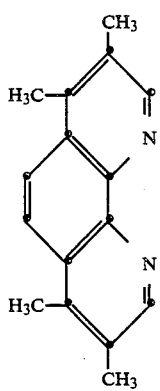
XIX
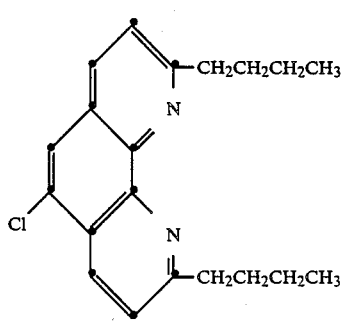
XX

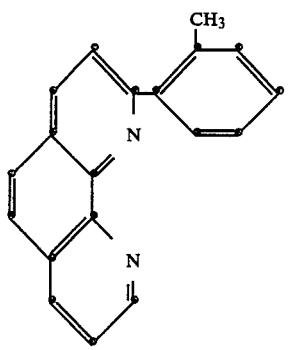
XXI
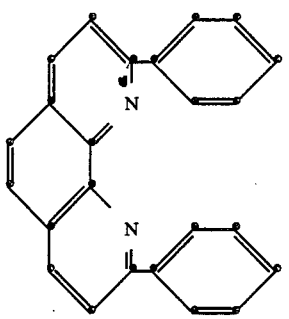
XXII
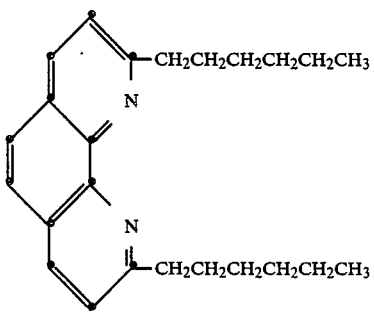
XXIII
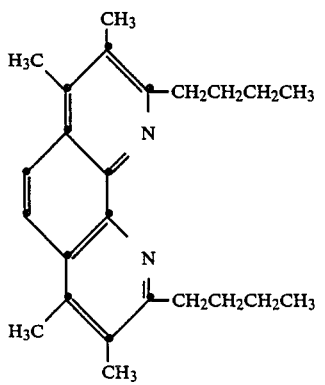
XXIV

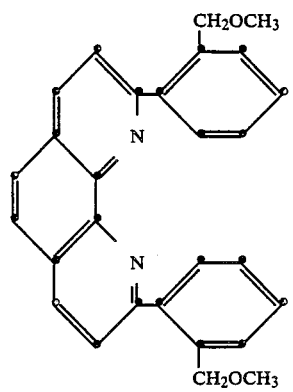
XXV
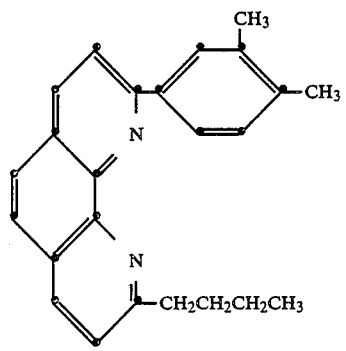
XXVI
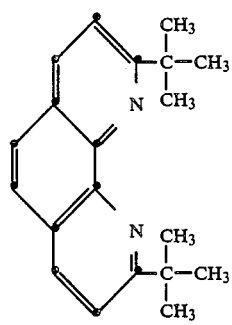
XXVII
25. The method of claim 19 wherein said supporting matrix is a hydrophobic binder.
26. The method of claim 19 carried out using a dry-operative lithium ion-selective electrode which comprises a dried internal reference element in contact with said membrane containing said phenanthroline.
* * * * *

UNITED STATES PATENT AND TRADEMARK OFFICE
CERTIFICATE OF CORRECTION

PATENT NO. : 4,853,090
DATED : August 1, 1989
INVENTOR(S) : Daniel S. Daniel et al It is certified that error appears in the above-identified patent and that said Letters Patent is hereby corrected as shown below:

Col. 1, line 7, the part reading

"U.S.S.N. 188,519,"

Should read

--U.S.S.N. 188,579,--.

Signed and Sealed this

Third Day of April, 1990

Attest:

HARRY F. MANBECK, JR.

*Attesting Officer*  *Commissioner of Patents and Trademarks*